United States Patent [19]
Taylor

[11] Patent Number: 5,797,864
[45] Date of Patent: *Aug. 25, 1998

[54] MULTI-PURPOSE BRACE

[75] Inventor: Dean A. Taylor, Vancouver, Canada

[73] Assignee: Generation II Orthotics, Inc., Richmond, Canada

[ * ] Notice: The term of this patent shall not extend beyond the expiration date of Pat. No. 5,554,105.

[21] Appl. No.: 749,049

[22] Filed: Nov. 14, 1996

[51] Int. Cl.$^6$ .......................................... A61F 5/00
[52] U.S. Cl. .............................. 602/26; 128/898
[58] Field of Search .................. 602/5, 16, 20, 602/23, 26; 128/898

[56] References Cited

U.S. PATENT DOCUMENTS

| | | | |
|---|---|---|---|
| 3,581,741 | 6/1971 | Rosman | 602/16 |
| 4,296,744 | 10/1981 | Palumbo | 602/26 |
| 4,506,661 | 3/1985 | Foster | 602/26 |
| 4,554,913 | 11/1985 | Womack et al. | 602/16 |
| 4,633,867 | 1/1987 | Kausek et al. | 602/26 |
| 4,854,308 | 8/1989 | Drillio | 602/26 X |
| 4,941,462 | 7/1990 | Lindberg | 602/26 X |
| 5,277,697 | 1/1994 | France et al. | 602/26 X |
| 5,458,565 | 10/1995 | Tillinghast, III | 602/26 |

*Primary Examiner*—Linda C. M. Dvorak
*Attorney, Agent, or Firm*—Townsend and Townsend and Crew LLP

[57] ABSTRACT

A method of alleviating the effects of degeneration of the knee. A lateral force applied to the knee. Simultaneously the position of the patella is stabilized during the application of the lateral force. A brace is also described. The brace can be located on the leg of the wearer and can apply lateral force on the knee of the wearer. Simultaneously the brace acts to stabilize the patella of the wearer during the application of the lateral force.

12 Claims, 4 Drawing Sheets

MULTI-PURPOSE BRACE

FIELD OF THE INVENTION

This invention relates to a method of alleviating the effects of degeneration of the knee and to a brace able to carry out the method.

DESCRIPTION OF RELATED ART

U.S. Pat. No. 3,902,482 issued Sep. 2, 1975 was a seminal invention in braces. The patent relates to an orthopaedic brace attachable to a wearer's body on opposite sides of the body joint. The invention finds particular application in the bracing of the knee. There is a mechanical joint comprising a bearing plate at one end of each brace portion near the body joint. A link extends across the body joint and has a bearing plate on each end. The bearing plates of the link overlap the bearing plates of the brace portion to provide dual bearings. A pivot interconnects the bearing plates of each of the dual bearings. The pivot provides each of the dual bearings with a plurality of transverse pivotal axes. These axes are shiftable to accommodate the natural pivotal movement of the body joint.

One of the brace portions is thus movable away from and towards the other of the brace portions as the body joint is flexed and straightened.

Braces of this type have now achieved excellent acceptance. They can be custom made for a patient. They are light and unobtrusive. A recent development has been the provision of over the counter braces stemming from developments of the brace of the above U.S. patent. The great virtue of the brace of the above U.S. patent is that the pivot, although light and simple in construction, has an excellent ability to follow the relatively complex motion of the knee. This is a marked improvement over the braces that preceded it.

There have been continuing improvements in this art, all stemming from the brace of U.S. Pat. No. 3,902,482.

U.S. Pat. No. 5,277,698 issued Aug. 18, 1993 relates to a knee bracing method that reduces the effect of unicompartmental osteoarthritis. In this patent, force is applied to the knee on that side of the knee remote from the compartment having osteoarthritis as the knee moves to extension. The force is applied to a particular point, posterior of the normal axis of rotation of the knee.

The method of the above U.S. Patent was improved, at least for certain circumstances of its use, in U.S. Pat. No. 5,562,605 which provided a stabilizer for a force strap to ensure that the strap remains in position over the patient's femoral condyle. Work on the brace of U.S. Pat. No. 5,277,698 indicated that the brace was most effective when the force strap applied the force over the femoral condyle. Although the brace of U.S. Pat. No. 5,277,698 generally was satisfactory in this regard there were circumstances where the strap could move off the femoral condyle. U.S. Pat. No. 5,562,605 successfully addresses this problem.

U.S. Pat. No. 5,302,169 issued Apr. 12, 1994 relates to an orthopaedic knee brace having a pair of rigid arms secured to a wearer's body. A pivotal joint between the substantially rigid arms allows pivoting of the knee while supporting the knee. The invention of this patent is the provision of a joint means in the brace to allow controlled medial and lateral inclination of each substantially rigid arm relative to the pivotal joint. By this means the knee could be supported, particularly after high tibial osteotomy but also as a means of easing the effects of unicompartmental osteoarthritis. The arrangement was such that the brace could be adjusted to provide the appropriate support for the knee. This patent, and a subsequent patent, U.S. Pat. No. 5,400,806 issued Mar. 28, 1995, also relate to a method of bracing the knee of a patient to relieve unicompartmental osteoarthritis and of supporting the knee of a patient following high tibial osteotomy. In the method the inclination of the substantially rigid arms was adjusted, as necessary, to provide the required support at the required inclination.

U.S. Pat. No. 5,554,105 is directed to a patella stabilizer. The patella stabilizer is a brace to be received around the knee with a generally Y-shaped first support member in the brace. A relative rigid second support is also provided having a generally U-shaped opening. This device provides excellent support for the patella or kneecap.

Osteoarthritis of the knee is a progressive, degenerative disease which, as it advances, encompasses many aspects of the knee, particularly the medial, and lateral compartment and the patella femoral compartment, resulting in tri-compartmental osteoarthritis.

It is unclear whether the patella is affected as a first, second or third stage of tri-compartmental osteoarthritis. However, regardless of the order of degeneration, at some stage the patella is affected and the present invention is based on the realization that the patella will benefit from treatment in combination with the other compartment most severely degenerated. Thus the present invention is a device for, and a method of, treating unicompartmental medial or unicompartmental lateral osteoarthritis in combination with patella femoral osteoarthritis.

Mechanically the patella tracks in the intracondylar notch in the femur as the leg moves during the gait cycle. Muscle firing during gait or other physical activity tends to pull the patella medially and then laterally with varying intensity. With increased intensity, lateral loads tends to increase, pulling the patella more severely from side to side, effectively stressing the patella femoral joint and resulting in increased pain and swelling with a knee that is degenerating.

A normal patella is able to withstand the loads caused by activity without painful results. However an abnormal patella, where the undersurfaces have degenerated, becomes painful as activity increases.

SUMMARY OF THE INVENTION

Accordingly, in a first aspect, the present invention is a method of alleviating the effects of degeneration of the knee that comprises:

applying a lateral force to the knee; and stabilizing the position of the patella during the application of the lateral force.

In a second aspect the present invention is a brace comprising:

means to locate the brace on the leg of the wearer;

means to apply lateral force to the knee of the wearer; and means to stabilize the patella of the wearer during the application of the lateral force.

DESCRIPTION OF PREFERRED EMBODIMENTS

The drawings show a brace having an upper cuff 10 and a lower cuff 12. The upper cuff 10 fits around the thigh of a wearer and the lower cuff 12 around the calf. The upper cuff 10 is attached to a rigid first arm 14 and a second rigid arm 16 is attached to the lower cuff 12. There is a pivotal joint 18 between the arms 14 and 16 that allows pivoting of the knee even when the brace is present. The pivotal joint 18 is known, for example, in the prior patents discussed above, the disclosures of which are hereby specifically incorporated by reference.

There are straps 20 extending around the leg of the wearer. These straps 20 extend from the cuffs. The brace of the present invention is secured to a wearer's body by use of the cuffs 10 and 12 in conjunction with the straps 20. There is also a central strap 22. The brace is formed as a sleeve provided with an opening 26 at its front to fit over the kneecap of a wearer.

The above structure may be considered part of the prior art.

Figure 1:
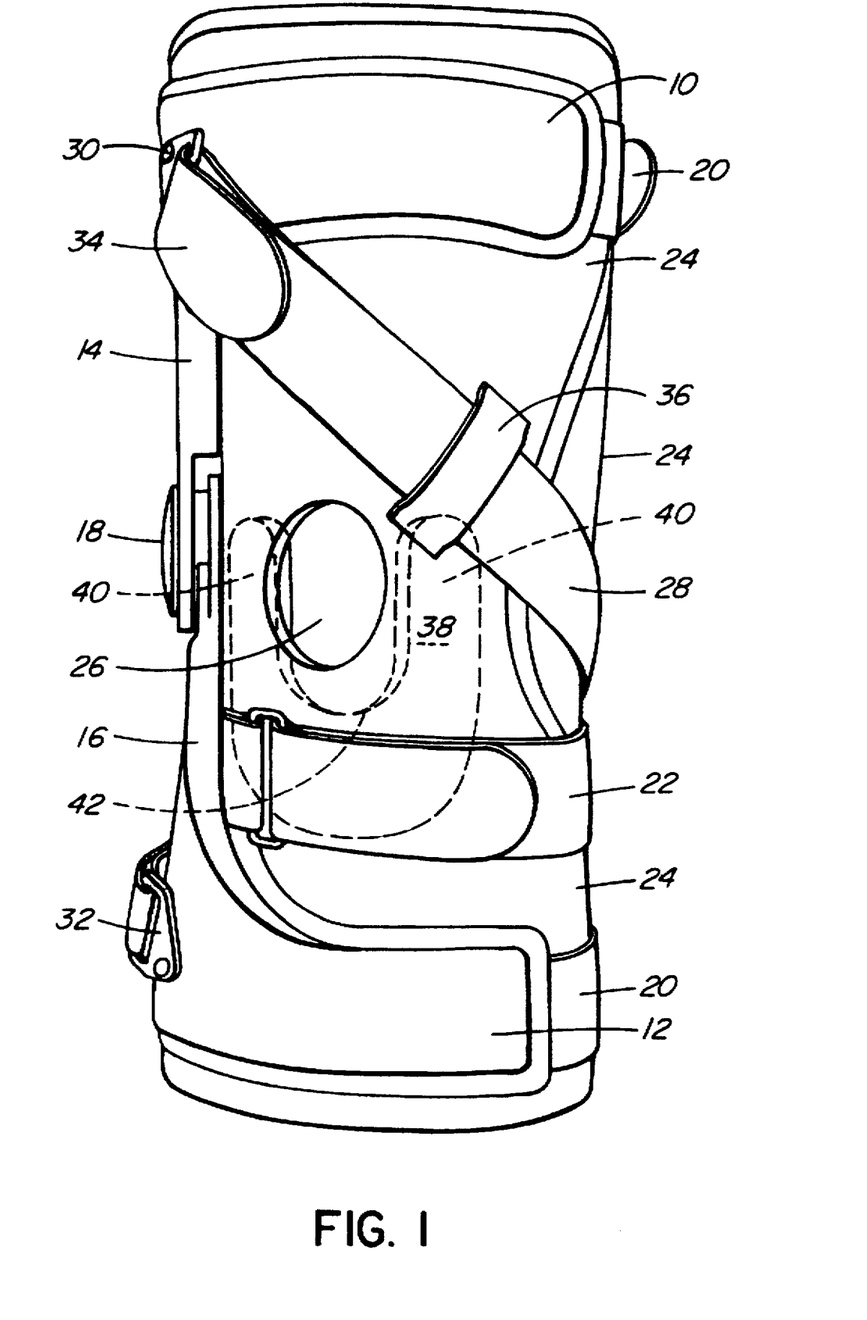
FIG. 1 is a front view of the brace according to the present invention.
Figure 2:
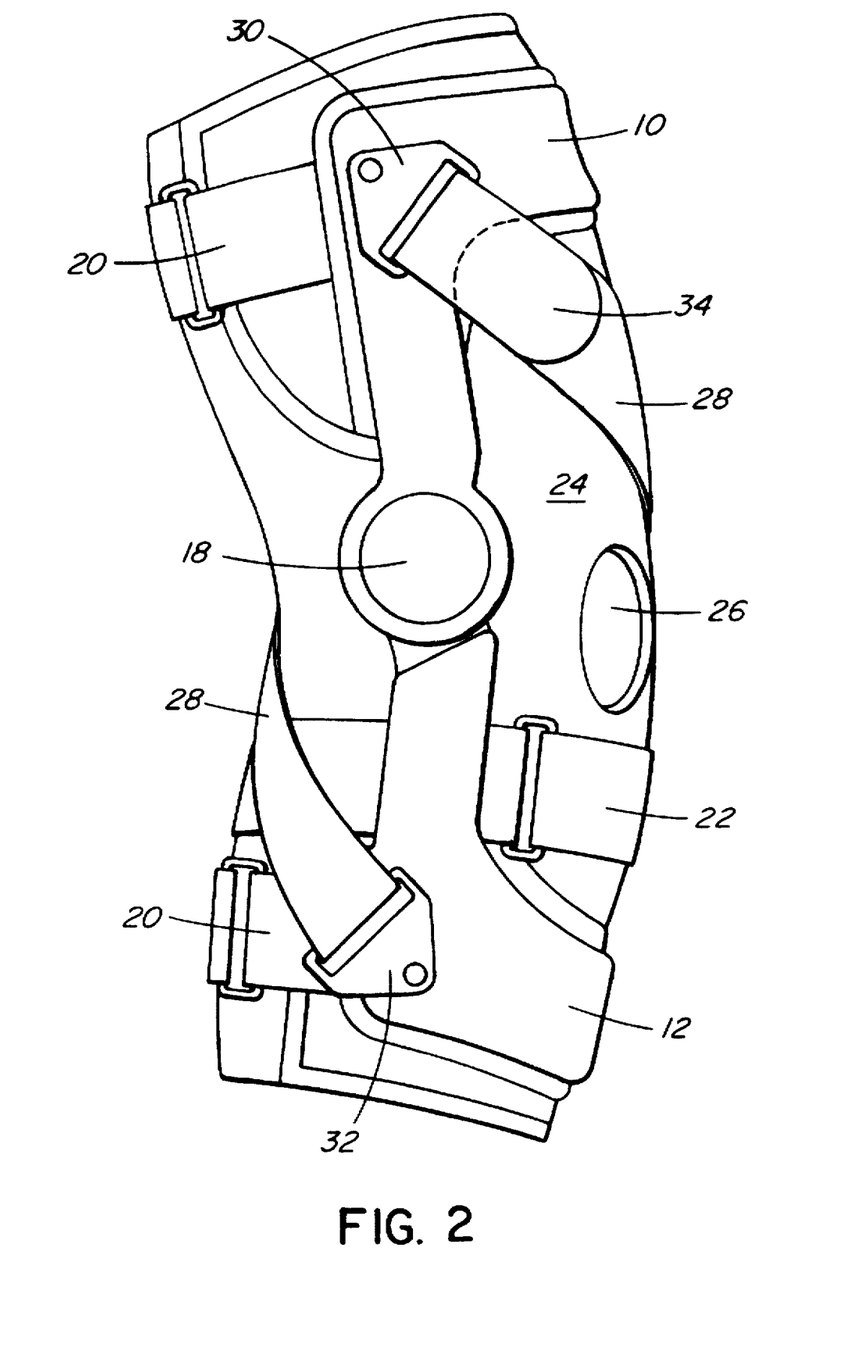
FIG. 2 is a side elevation of the brace of FIG. 1.
Figure 3:
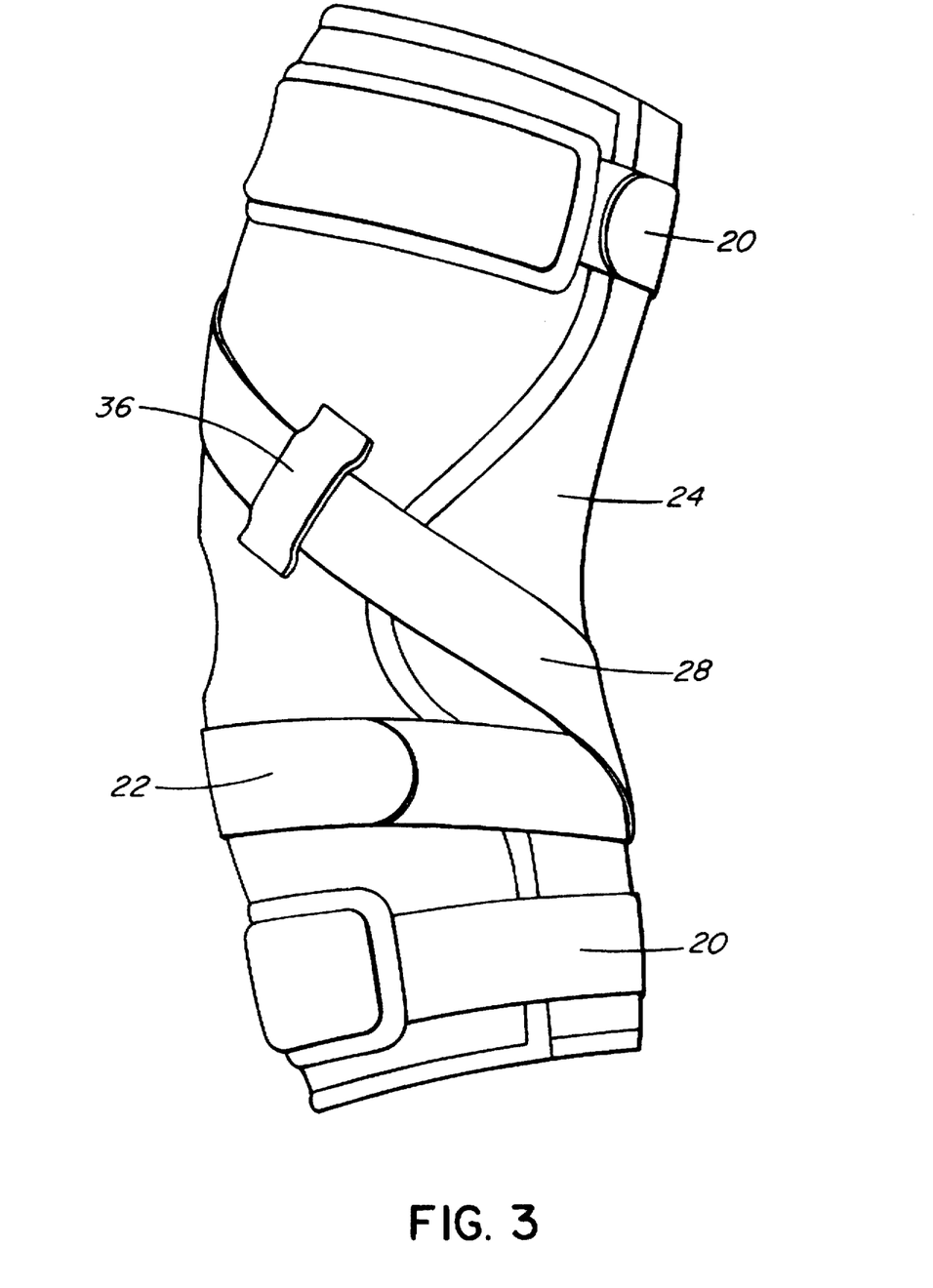
FIG. 3 is a further side elevation of the brace of FIG. 1, from the side different from that of FIG. 2.

The embodiment of FIGS. 1 to 3 shows a force strap 28 extending from a first anchor 30 on the upper cuff 10 to a second anchor 32 on the lower cuff 12. These anchors are pivotally mounted to the respective cuffs. Although not shown in detail the force strap has pile and hook anchors, for example those available under the trademark Velcro at its end 34 so that the strap 28, once fed through the upper anchor 30, can feed back on itself and be fastened. By this means a substantial force can be exerted. The illustrated brace is for a right leg and the force strap 28 applies lateral force to the inner compartment of the knee. A simple loop 36 acts to ensure that the force strap 28 remains over the wearer's femoral condyle.

The brace has a buttress 38 of generally U-shaped configuration with its limbs 40 extending on either side of the kneecap and its base 42 below or inferior to the kneecap.

Although the buttress 38 is shown in conventional U position in fact the U may be moved through 90° to either side so that the base 42 is medial or lateral relative to the patella or even through 180° so that base 42 is superior to the patella. The last is relatively rare.

Using the brace of FIGS. 1 to 3 force is applied laterally to the knee by the force strap 28. As the force is applied, according to the requirement of the patient, to adjust the loading on the knee compartment remote from the force strap 28, that is to say adjacent the hinge 18, the buttress 38 supports the patella of the wearer. The arrangement is such that excellent support for the patella is provided simultaneously with the application of an alleviating lateral force to the knee.

Thus according to the method of the present invention, to use the brace of FIGS. 1 to 3, a lateral force is applied to the knee by tightening the strap 28 simply by pulling on the end 34 of the strap and fastening it back on itself using the Velcro fastener. While the force is applied in this way the patella is stabilized by the buttress 38.

The brace of the present invention may also include the arrangements shown in U.S. Pat. Nos. 5,302,169 and 5,400,806 discussed above. An example is shown in FIG. 4.

Figure 4:
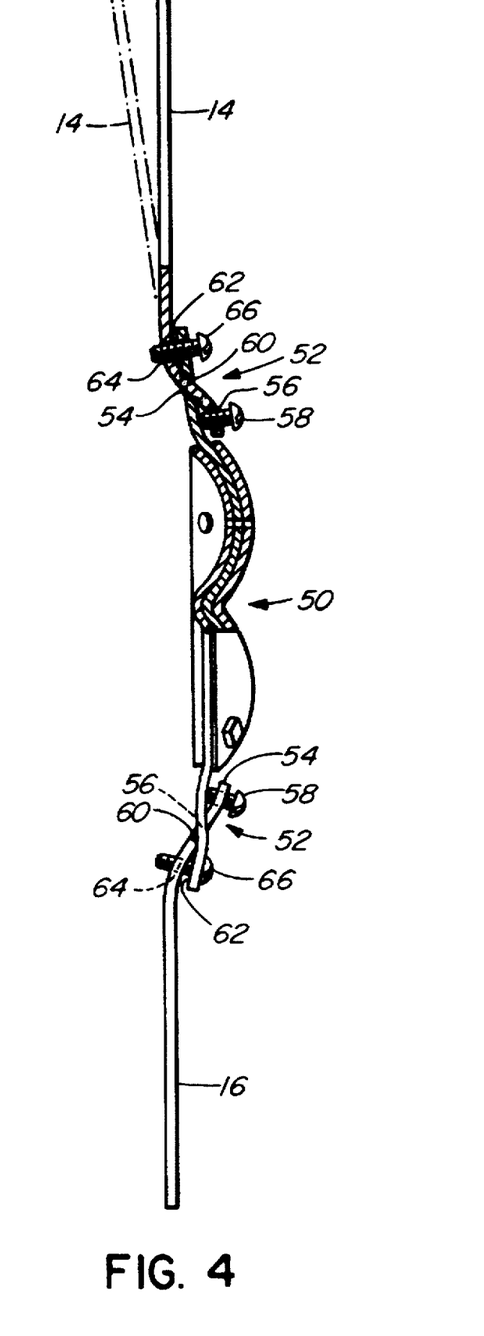
FIG. 4 is a detail of a further embodiment.

FIG. 4 shows the substantially rigid arms 14 and 16 interconnected by a pivotable joint 50. Pivotable joint 50 is known in the art. It is described, for example, in detail in U.S. Pat. No. 5,400,806, the disclosure of which is specifically incorporated herein by reference.

Arms 14 and 16 may be considered to be broken into two parts. There is a joint 52 in each arm 14 or 16. The joint 52 allows controlled inclination of the outer, greater part of each arm 14 or 16 relative to the pivotable joint 50.

There is a tab 54 on the outer part of arms 14 and 16, adjacent the pivotable joint 50. Tab 54 has a threaded opening 56 that receives a screw 58. There is an opening 60 in the inner shorter parts of the arms 14 and 16 that receives tab 54. The first and second parts of the arms are thus secured together and can be locked in a predetermined position. Screws 58 provide means to move the first and second parts relative to each other to set the predetermined position. The parts of arms 14 and 16 are secured together by clear opening 62 in the inner parts of the arms 14 and 16, adjacent the opening 60 through which the tab 54 extends. There is a threaded opening 64 to receive a screw 66.

To use the embodiment of FIG. 4 the screws 66 are loosened which means that the outer parts of each arm 14 and 16 can move relative to the inner part of the arms. The screws 58 might also be slackened if required. Once the screws 66 are loose the brace may be placed on the leg of the wearer. The screws 58 tighten in openings 56 until screw 58 makes contact with the inner part of the arm 14 or 16. When the correct position is established in this way the screws 66 will be tightened to secure that position. Thus the screws 58 and 66 can be used in conjunction to ensure that a lateral force is applied to the knee by movement of the rigid arms 14 and 16. Movement of arm 14 is illustrated in broken lines in the top part of FIG. 4.

Again with this embodiment the buttress 38 secures the patella during application of the lateral force.

In both embodiments the effect of the lateral force is to open up the joint compartment that is, through degeneration, closing together. That is to say the lateral force acts to restore the joint to a position that more closely resembles a healthy joint. Lateral force is, generally speaking, applied in the coronal plane of the knee.

Although the present invention has been described in some detail by way of illustration and example for purposes of clarity and understanding, it will be readily apparent to those of ordinary skill in the art in light of the teachings of this invention that certain changes and modifications may be made thereto without departing from the spirit or scope of the appended claims.

I claim:

1. A method of alleviating the effects of degeneration of the knee in which the degeneration involves the patella and at least one of the medial and lateral compartments of the knee, the method comprising:

applying a lateral force to the knee; and stabilizing the position of the patella during the application of the lateral force.

2. A method as claimed in claim 1 in which the lateral force is supplied by a brace received around the knee.

3. A method as claimed in claim 2 in which the brace has adjustable means to allow application and variation of the lateral force.

4. A method as claimed in claim 1 in which the brace comprises a sleeve;

means to secure the sleeve around the knee including cuffs to be located above and below the knee;

substantially rigid arms extending from each cuff to a hinge; and a force strap able to extend from one cuff to the other cuff, around the knee, whereby the tightening of the strap applies lateral force to the knee of the wearer.

5. A method as claimed in claim 1 in which the patella is stabilized by a generally U-shaped buttress able to fit under and alongside the patella.

6. A method as claimed in claim 1 in which the buttress is anchored within the brace.

7. A brace comprising:

means to locate the brace on the leg of the wearer;

means to apply lateral force to the knee of the wearer; and means to stabilize the patella of the wearer during the application of the lateral force.

8. A brace as claimed in claim 7 in which the means to locate the brace on the leg of a wearer comprises cuffs to be located above and below the knee of the wearer;

straps extending around the brace to ensure positive location of the brace.

9. A brace as claimed in claim 7 in which the means to apply lateral force to the knee of the wearer comprises a force strap able to extend from a point above the knee, around the knee, to a point below the knee, whereby tightening of the strap applies lateral force to the knee.

10. A brace as claimed in claim 7 in which the lateral force is applied by the provision of substantially rigid limbs extending above and below the knee to location points on the brace;

a hinge to be located generally adjacent the knee;

means within the substantially rigid arms to allow controlled inclination of each relatively rigid arm relative to the pivotable joint and thus to apply lateral force to the knee.

11. A brace as claimed in claim 7 in which the means to stabilize the patella of the wearer during the application the lateral force comprises a generally U-shaped buttress adapted to be received beneath and around the knee.

12. A brace as claimed in claim 11 in which the buttress is attached to interior of the brace.

* * * * *

UNITED STATES PATENT AND TRADEMARK OFFICE
CERTIFICATE OF CORRECTION

PATENT NO.       : 5,797,864
APPLICATION NO. : 08/749049
DATED            : November 14, 1996
INVENTOR(S)      : Dean Taylor It is certified that error appears in the above-identified patent and that said Letters Patent is hereby corrected as shown below:

On The Title Page, Item (56)
References Cited - U.S. Patent Documents,

Please Add the following references

| | | |
|---|---|---|
| 3,902,482 | 9/2/75   | Taylor |
| 5,277,689 | 1/11/94  | Taylor |
| 5,302,169 | 4/12/94  | Taylor |
| 5,356,370 | 10/18/94 | Fleming |
| 5,400,806 | 3/28/95  | Taylor |
| 5,457,891 | 10/17/95 | Taylor |
| 5,554,105 | 9/10/96  | Taylor |
| 5,562,605 | 10/8/96  | Taylor |

Signed and Sealed this

First Day of August, 2006

JON W. DUDAS
*Director of the United States Patent and Trademark Office*

UNITED STATES PATENT AND TRADEMARK OFFICE
CERTIFICATE OF CORRECTION

PATENT NO.         : 5,797,864
APPLICATION NO. : 08/749049
DATED                 : August 25, 1998
INVENTOR(S)       : Dean Taylor Page 1 of 1

It is certified that error appears in the above-identified patent and that said Letters Patent is hereby corrected as shown below:

On The Title Page, Item (56)
References Cited - U.S. Patent Documents,

Please Add the following references

| | | |
|---|---|---|
| 3,902,482 | 9/2/75   | Taylor |
| 5,277,689 | 1/11/94  | Taylor |
| 5,302,169 | 4/12/94  | Taylor |
| 5,356,370 | 10/18/94 | Fleming |
| 5,400,806 | 3/28/95  | Taylor |
| 5,457,891 | 10/17/95 | Taylor |
| 5,554,105 | 9/10/96  | Taylor |
| 5,562,605 | 10/8/96  | Taylor |

This certificate supersedes Certificate of Correction issued August 1, 2006

Signed and Sealed this

Tenth Day of October, 2006

JON W. DUDAS
*Director of the United States Patent and Trademark Office*

US005797864C1

(12) EX PARTE REEXAMINATION CERTIFICATE (5567th)
United States Patent
Taylor (10) Number: US 5,797,864 C1
(45) Certificate Issued: Oct. 17, 2006

(54) MULTI-PURPOSE BRACE

(75) Inventor: Dean A. Taylor, Vancouver (CA)

(73) Assignee: Generation II Orthotics, Inc., Richmond (CA)

Reexamination Request:
No. 90/007,330, Dec. 3, 2004

Reexamination Certificate for:
Patent No.: 5,797,864
Issued: Aug. 25, 1998
Appl. No.: 08/749,049
Filed: Nov. 14, 1996

(51) Int. Cl.
*A61F 5/01* (2006.01)

(52) U.S. Cl. .................................. 602/26; 128/898
(58) Field of Classification Search .................. None
See application file for complete search history.

(56) References Cited

U.S. PATENT DOCUMENTS

| | | | |
|---|---|---|---|
| 3,786,804 A | * | 1/1974 | Lewis .................. 602/16 |
| 3,902,482 A | | 9/1975 | Taylor |
| 4,941,462 A | * | 7/1990 | Lindberg ............... 602/16 |
| 5,277,698 A | * | 1/1994 | Taylor .................. 602/26 |
| 5,302,169 A | * | 4/1994 | Taylor .................. 602/26 |
| 5,356,370 A | | 10/1994 | Fleming |
| 5,400,806 A | | 3/1995 | Taylor |
| 5,451,201 A | * | 9/1995 | Prengler ............... 602/26 |
| 5,457,891 A | | 10/1995 | Taylor |
| 5,554,105 A | | 9/1996 | Taylor |
| 5,562,605 A | * | 10/1996 | Taylor .................. 602/26 |
| 5,873,848 A | * | 2/1999 | Fulkerson ............. 602/62 |

* cited by examiner

*Primary Examiner*—Peter English (57) ABSTRACT

A method of alleviating the effects of degeneration of the knee. A lateral force applied to the knee. Simultaneously the position of the patella is stabilized during the application of the lateral force. A brace is also described. The brace can be located on the leg of the wearer and can apply lateral force on the knee of the wearer. Simultaneously the brace acts to stabilize the patella of the wearer during the application of the lateral force.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 3, 5 and 9–12 are cancelled.

Claims 1, 2, 4 and 6–8 are determined to be patentable as amended.

New claim 13 is added and determined to be patentable.

1. A method of alleviating the effects of degeneration of the knee in which the degeneration involves the patella and at least one of the medial and lateral compartments of the knee, the method comprising:
   applying a lateral force to the knee *with a force strap able to extend around the knee, whereby the tightening of the strap applies a lateral force to a degenerated compartment of the knee*; and
   stabilizing the position of the patella during the application of the lateral force *with a generally U-shaped buttress able to fit under and alongside the patella*.

2. A method as claimed in claim 1 in which the [lateral force] *force strap* is [supplied] *supported* by a brace received around the knee.

4. A method as claimed in claim [1] *2* in which the brace comprises a sleeve[:]
   [means to secure the sleeve around the knee including] *and* cuffs to be located above and below the knee *to secure the brace around the knee*; and
   substantially rigid arms extending from each cuff to a hinge[; and
   a force strap able to extend from one cuff to the other cuff, around the knee, whereby the tightening of the strap applies lateral force to the knee of the wearer].

6. A method as claimed in claim [1] *2* in which the buttress is anchored within the brace.

7. A brace *for alleviating the effects of degeneration of the knee in which the degeneration involves the patella and at least one of the medial and lateral compartments of the knee,* comprising:
   means to locate the brace on the leg of the wearer;
   [means to apply lateral force to the knee of the wearer] *a force strap able to extend from a point above the knee, about the knee, to a point below the knee, whereby tightening of the strap applies lateral force to a degenerated compartment of the knee*; and
   [means] *a generally U-shaped buttress adapted to be received beneath and around the knee* to stabilize the patella of the wearer during the application of the lateral force *from the strap, the buttress being attached to the interior of the brace.*

8. A brace as claimed in claim 7 in which the means to locate the brace on the leg of [a] *the* wearer comprises cuffs to be located above and below the knee of the wearer;
   straps extending around the brace to ensure positive location of the brace.

*13. A brace for alleviating the effects of degeneration of the knee in which the degeneration involves the patella and at least one of the medial and lateral compartments of the knee, comprising:*
   *means to locate the brace on the leg of the wearer;*
   *substantially rigid arms extending above and below the knee to location points on the brace;*
   *a pivotable joint to be located generally adjacent the knee;*
   *a joint within each of the substantially rigid arms to allow controlled inclination of each substantially rigid arm relative to the pivotable joint and thus to apply lateral force to a degenerated compartment of the knee; and*
   *a generally U-shaped buttress adapted to be received beneath and around the knee to stabilize the patella of the wearer during the application of the lateral force from the arms, the buttress being attached to the interior of the brace.*

* * * * *